United States Patent
Vu

[19]

[11] Patent Number: 6,135,980
[45] Date of Patent: Oct. 24, 2000

[54] MUCUS SUCTION DEVICE

[76] Inventor: Denis A. Vu, 239 Alphine Dr., Rochester, N.Y. 14618

[21] Appl. No.: 09/375,222

[22] Filed: Aug. 16, 1999

[51] Int. Cl.⁷ .................................................. A61M 1/06
[52] U.S. Cl. ............................................. 604/73; 604/315
[58] Field of Search ................................ 604/30, 35, 36, 604/48, 514, 73, 74, 131, 133, 146, 149, 151, 153, 313–316, 540, 328; 128/205.19

[56] References Cited

U.S. PATENT DOCUMENTS

| | | | |
|---|---|---|---|
| 4,799,924 | 1/1989 | Rosenblatt | 604/181 |
| 4,813,931 | 3/1989 | Hauze | 604/54 |
| 4,995,386 | 2/1991 | Ng | 128/205.19 |
| 5,024,653 | 6/1991 | Kohnke | 604/35 |
| 5,098,386 | 3/1992 | Smith | 604/152 |
| 5,098,418 | 3/1992 | Maitz et al. | 604/319 |
| 5,183,467 | 2/1993 | Mouney | 604/149 |
| 5,318,548 | 6/1994 | Filshie | 604/319 |
| 5,496,268 | 3/1996 | Perla | 604/27 |
| 5,782,837 | 7/1998 | York | 606/106 |
| 5,899,878 | 5/1999 | Glassman | 604/48 |

*Primary Examiner*—Sharon Kennedy
*Attorney, Agent, or Firm*—Robert J. Bird

[57] ABSTRACT

A mucus suction device includes a pump housing, collection vessel connected to the pump housing, and a fluid conduit connected to the vessel and adapted for placement in a nostril. The pump housing, vessel, and conduit together define an air path. The pump housing encloses a flexible diaphragm and a motor to pulsate it. Behind the diaphragm is an air chamber communicating with the fluid conduit and with a discharge passage to atmosphere. The collection vessel includes a first nipple for connection with the conduit and a second nipple for connection with the air chamber. The fluid conduit includes a mucus tube for placement into a nostril. The air path also includes check valve, one between the tube and the air chamber, and the other between the air chamber and the discharge passage. Pulsation of the diaphragm moves air through the discharge passage and generates vacuum pressure in the fluid conduit to draw mucus into the fluid conduit.

5 Claims, 2 Drawing Sheets

MUCUS SUCTION DEVICE

BACKGROUND OF THE INVENTION

This invention is a device for removing mucus from the nostils of infants, toddlers, and others who are unable to expel mucus by themselves.

The well known rubber syringe is the only relevant prior art that I know. A rubber syringe takes in fluid when its bulbous portion, after being squeezed or compressed, is relaxed to return to its normal configuration. The suction or vacuum pressure created at the tube end of such a syringe is approximately 0.25 mm Hg.

SUMMARY OF THE INVENTION

A mucus suction device according to this invention includes a pump housing, collection vessel connected to the pump housing, and a fluid conduit connected to the vessel and adapted for placement in a nostril. The pump housing, vessel, and conduit together define an air path. The pump housing encloses a flexible diaphragm and a motor to pulsate it. Behind the diaphragm is an air chamber communicating with the fluid conduit and with a discharge passage to atmosphere. The collection vessel includes a first nipple for connection with the conduit and a second nipple for connection with the air chamber. The fluid conduit includes a mucus tube for placement into a nostril. The air path also includes check valve, one between the tube and the air chamber, and the other between the air chamber and the discharge passage. Pulsation of the diaphragm moves air through the discharge passage and generates vacuum pressure in the fluid conduit to draw mucus into the fluid conduit.

DETAILED DESCRIPTION

Figure 2:
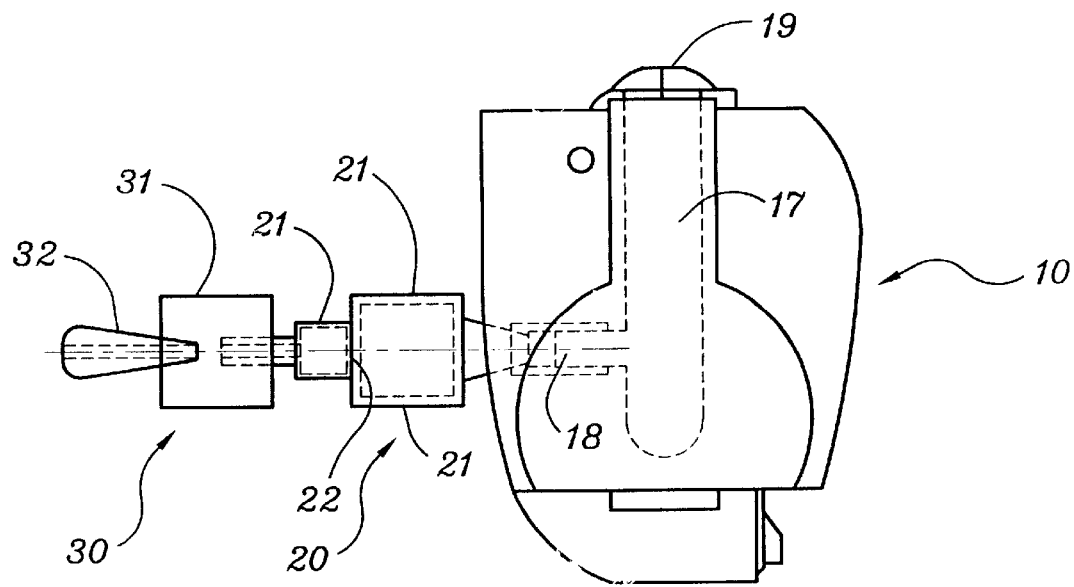
FIG. 2 is a top view of the device shown in FIG. 1.
Figure 1:
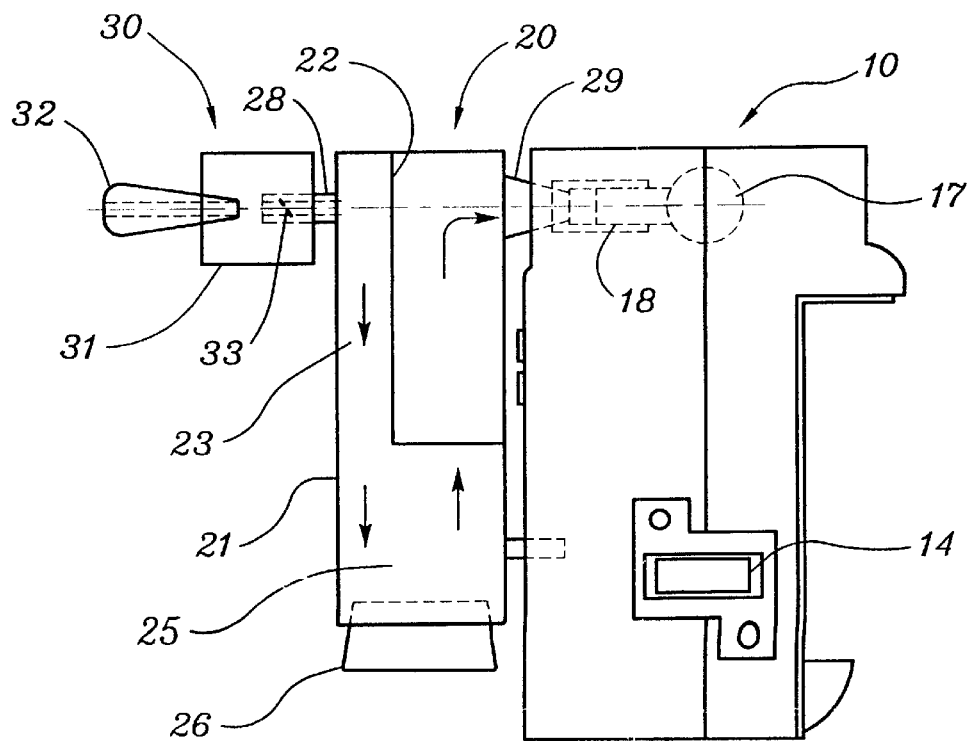
FIG. 1 is a side elevation view of the suction device of this invention.

Referring to FIGS. 1, 2, the suction device of this invention includes a pump housing 10, a collection vessel 20 removably connected to the pump housing 10, and a fluid conduit 30 removably connected to the vessel 20.

Figure 3:
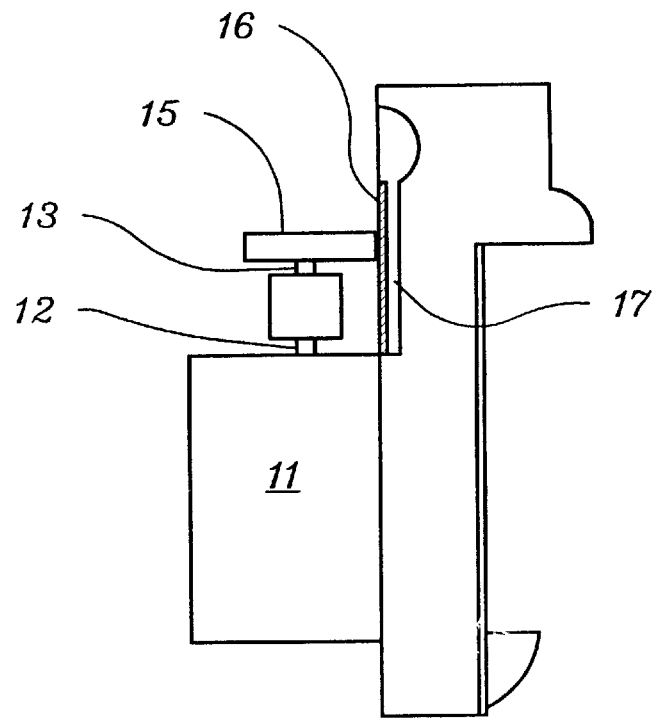
FIG. 3 is an elevation view of a part of FIG. 1, separated from the rest of FIG. 1 at parting line A.
Figure 4:
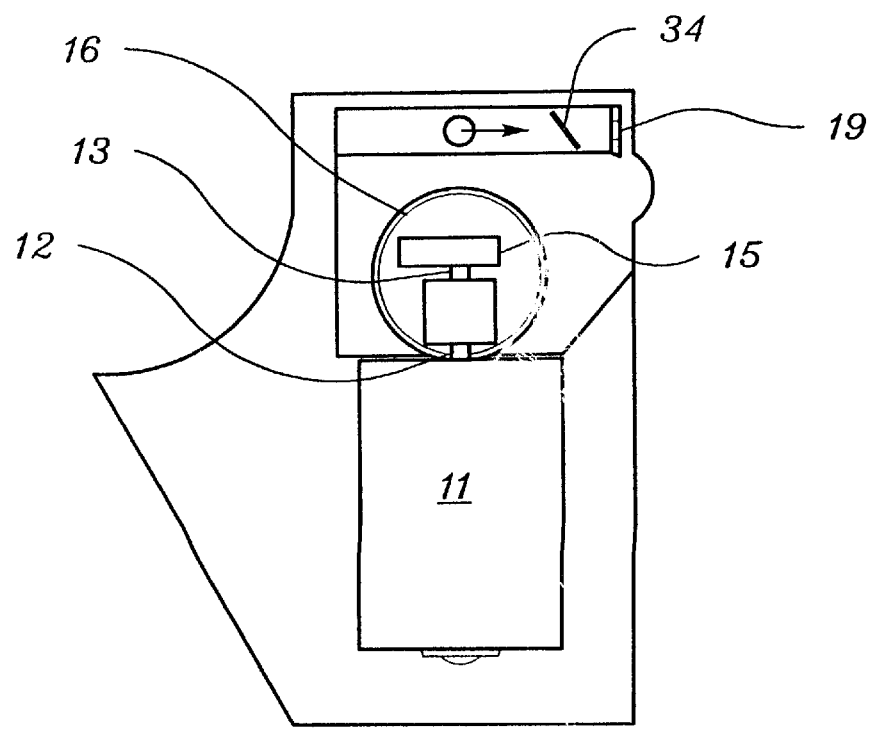
FIG. 4 is a left side view of FIG. 3.

The pump housing 10 encloses a motor 11 which is connected to a battery or other DC source (not shown) and to an on-off switch 14 mounted on an outside wall of the pump housing 10. FIGS. 3, 4 show the motor 11 including a drive shaft 12, an eccentric spindle 13 on the drive shaft, and a rotatable roller 15 on the spindle 13. The roller 15 bears against a flexible diaphragm 16 mounted over an air chamber 17.

The collection vessel 20 includes transparent sidewalls 21 and an internal partition 22 dividing the vessel into first and second vertical channels 23, 24 with a common bottom chamber 25. The channels 23, 24 and bottom chamber 25 together form a U-shaped vessel. The bottom of the chamber 25 is accessible for cleaning and the like by means of a removable plug 26. The vessel 20 includes a first nipple 28 for removable connection with the conduit 30, and a second nipple 29 for removable connection with an internal passage 18 in the pump housing 10. The passage 18 leads into the air chamber 17 behind the diaphragm 16 and through a discharge aperture 19 in the pump housing 10, to atmosphere.

The conduit 30 includes a flexible tube 31 with a probe or tip 32 on its end for placement into the nostrils for removal of mucus.

In operation, with the tip 32 placed at a nostril opening, the motor 11 is actuated by the switch 14. The pulsating action of the diaphragm 16, moving in and out with the eccentric-driven roller 15, pushes air to atmosphere from the air chamber 17, generating a suction or vacuum pressure in the passage 18 and conduit 30. Mucus is thereby drawn into the tip 32 of the conduit 30 and into the collection vessel 20. The fluid flow path within the vessel 20 is down through the first channel 23, through the bottom chamber 25, and up through the second channel 24, as indicated by arrows in FIG. 1. The suction or vacuum pressure generated by this device is approximately 5.0 mm Hg.

Air is "pumped" through the system by a reciprocating or pulsating diaphragm 16. The system therefore includes check valves, one upstream and one downstream of the air chamber 17, so that air is not simply pushed back and forth with every in-out cycle of the diaphragm. A first check valve 33 is located in the air path between the tip 32 and the air chamber 17, preferably in either the first nipple 28 (as shown in FIG. 1) or the second nipple 29 of the collection vessel 20. A second check valve 34 is shown in the discharge aperture 19.

The foregoing description of a preferred embodiment of this invention, including any dimensions, angles, or proportions, is intended as illustrative. The concept and scope of the invention are limited only by the following claims and equivalents thereof.

What is claimed is:

1. A mucus suction device, including a pump housing, a collection vessel removably connected to said pump housing, and a fluid conduit connected to said vessel and adapted for placement in a nostril, said pump housing, vessel, and conduit together defining an air path;

said pump housing enclosing a flexible diaphragm, means to pulsate said diaphragm, and an air chamber on one side of said diaphragm, said air chamber communicating with said fluid conduit and with a discharge passage to atmosphere;

said collection vessel including a first nipple for removable connection with said conduit and a second nipple for removable connection with said air chamber;

said fluid conduit including a mucus tube adapted for placement into a nostril;

a first check valve in said air path between said tube and said air chamber; and a second check valve in said air path between said air chamber and said discharge passage;

whereby said diaphragm is pulsated to move air through said discharge passage and generate vacuum pressure in said fluid conduit to thereby draw mucus into said fluid conduit.

2. A mucus suction device, including a pump housing, a collection vessel removably connected to said pump housing, and a fluid conduit connected to said vessel and adapted for placement in a nostril, said pump housing, said vessel, and said conduit together defining an air path;

said pump housing enclosing a motor, a drive shaft on said motor, an eccentric member on said drive shaft bearing against one side of a flexible diaphragm, and an air chamber on the other side of said diaphragm, said air chamber communicating with said fluid conduit and with a discharge passage to atmosphere;

said collection vessel including a U-shaped fluid path with a first nipple for removable connection with said conduit and a second nipple for removable connection with said air chamber;

said fluid conduit including a tube adapted for placement into a nostril for removal of mucus therefrom;

a first check valve in said air path between said tube and said air chamber; and a second check valve in said air path between said air chamber and said discharge passage;

whereby said diaphragm is pulsated to move air through said discharge passage and generate vacuum pressure in said fluid conduit to thereby draw mucus into said fluid conduit.

3. A mucus suction device, including a pump housing, a collection vessel removably connected to said pump housing, and a fluid conduit connected to said vessel and adapted for placement in a nostril, said pump housing, said collection vessel, and said fluid conduit together defining an air path;

said pump housing enclosing a motor, a drive shaft on said motor, a spindle eccentrically mounted on said drive shaft, a roller rotatably mounted on said spindle and bearing against one side of a flexible diaphragm, and an air chamber on the other side of said diaphragm, said air chamber communicating with said fluid conduit and with a discharge passage to atmosphere;

said collection vessel including a U-shaped fluid path with a first nipple for removable connection with said conduit and a second nipple for removable connection with said air chamber;

said fluid conduit including a tube adapted for placement into a nostril for removal of mucus therefrom;

a first check valve in said air path between said tube and said air chamber; and a second check valve in said air path between said air chamber and said discharge passage;

whereby said diaphragm is pulsated to move air through said discharge passage and generate vacuum pressure in said fluid conduit to thereby draw mucus into said fluid conduit.

4. A device as defined in claim 3 in which said first check valve is in said first nipple.

5. A device as defined in claim 3 in which said first check valve is in said second nipple.

* * * * *